US006696023B2

(12) United States Patent
Grimm et al.

(10) Patent No.: US 6,696,023 B2
(45) Date of Patent: Feb. 24, 2004

(54) APPARATUS FOR IRRADIATION OF BLOOD PRODUCTS

(75) Inventors: Daniel J. Grimm, McHenry, IL (US); Mark S. Leuenberger, Gurnee, IL (US)

(73) Assignee: Baxter International Inc., Deerfield, IL (US)

(*) Notice: Subject to any disclaimer, the term of this patent is extended or adjusted under 35 U.S.C. 154(b) by 12 days.

(21) Appl. No.: 09/849,837

(22) Filed: May 4, 2001

(65) Prior Publication Data

US 2001/0024623 A1 Sep. 27, 2001

Related U.S. Application Data

(62) Division of application No. 08/121,820, filed on Sep. 15, 1993, now Pat. No. 6,245,570, which is a division of application No. 08/058,996, filed on May 6, 1993, now abandoned, which is a continuation of application No. 07/697,170, filed on May 8, 1991, now abandoned.

(51) Int. Cl.[7] ............................................. A61L 2/10
(52) U.S. Cl. ................ 422/99; 250/455.11; 250/492.1; 422/24; 422/104; 604/6.08
(58) Field of Search .......................... 422/24, 99, 104; 250/454.11, 455.11, 492.1, 453.11; 604/6.08

(56) References Cited

U.S. PATENT DOCUMENTS

| | | | |
|---|---|---|---|
| 2,693,169 A | 11/1954 | Ryan | |
| 3,371,897 A | 3/1968 | Serany, Jr. et al. | |
| 3,694,651 A | 9/1972 | Glasson | |
| 3,915,212 A | 10/1975 | Bujan et al. | |
| 4,062,713 A | 12/1977 | Anderson | |
| 4,121,714 A | 10/1978 | Daly et al. | |
| 4,296,066 A | * 10/1981 | Schenck | 422/24 |
| 4,433,244 A | 2/1984 | Hogan | |
| 4,448,750 A | 5/1984 | Fuesting | |
| 4,526,404 A | 7/1985 | Vazquez | |
| 4,561,110 A | 12/1985 | Herbert | |
| 4,608,255 A | 8/1986 | Kahn et al. | |
| 4,622,032 A | 11/1986 | Katsura et al. | |
| 4,657,541 A | 4/1987 | Ichikawa et al. | |
| 4,678,894 A | 7/1987 | Shafer | |
| 4,726,949 A | 2/1988 | Miripol et al. | |
| 4,748,120 A | 5/1988 | Wiesehahn | |
| 4,828,716 A | 5/1989 | McEwen et al. | |
| 4,857,713 A | 8/1989 | Brown | |
| 4,866,282 A | 9/1989 | Miripol et al. | |
| 4,882,496 A | 11/1989 | Bellotti et al. | |
| 4,896,042 A | 1/1990 | Humphreys | |
| D306,759 S | 3/1990 | D'Alo | |
| 4,952,812 A | 8/1990 | Miripol et al. | |
| 4,975,587 A | 12/1990 | Min-Jenn | |
| 4,976,708 A | 12/1990 | Oshiyama | |
| 4,994,039 A | 2/1991 | Mattson | |
| 5,006,050 A | 4/1991 | Cooke et al. | |
| 5,019,243 A | 5/1991 | McEwen et al. | |
| 5,116,316 A | 5/1992 | Sertic et al. | |
| 5,868,695 A | * 2/1999 | Wolf et al. | 604/6.08 |

FOREIGN PATENT DOCUMENTS

| | | |
|---|---|---|
| EP | 0 080 780 | 11/1982 |
| EP | 152072 | 8/1985 |
| EP | 392429 | 10/1990 |
| WO | WO 89/09067 | 3/1989 |
| WO | WO 89/09068 | 10/1989 |

OTHER PUBLICATIONS

Photocopy of Baxter Transfer Pack Container, Copyright notice of the year 1989.
Operator's Manual–Fenwal Ultraviolet Irradiation System Copyright 1990.

* cited by examiner

*Primary Examiner*—Jan Ludlow
(74) *Attorney, Agent, or Firm*—Andrew Kolomayets; Michael C. Mayo

(57) ABSTRACT

An apparatus for irradiating materials is disclosed. The apparatus includes a housing defining a chamber and a pair of light sources positioned on opposite sides of the chamber. The housing includes a pair of housing sections moveable in hinged relation between open and closed positions. A manually removable tray within the housing to define a support suface for a flexible container in the chamber is also provided.

4 Claims, 2 Drawing Sheets

APPARATUS FOR IRRADIATION OF BLOOD PRODUCTS

This application is a divisional of U.S. application Ser. No. 08/121,820, filed Sep. 15, 1993, now U.S. Pat. No. 6,245,570, which is a division of application Ser. No. 08/058,996, filed May 6, 993, abandoned, which is a continuation of U.S. application Ser. No. 07/697,170, filed May 8, 1991, abandoned.

TECHNICAL FIELD

As described in Kahn et al. U.S. Pat. No. 4,608,255 entitled Biocompatible Method for in Situ Production of Functional Platelets and Product Produced Thereby Lacking Immunogenicity, it is taught to expose blood products which contain substantial numbers of platelets to ultraviolet (U.V.) radiation, to eliminate or greatly decrease an immune response to the platelet preparation by alloimmunized patients. It is generally believed that this alloimmunization is caused by the residual lymphocytes present in the platelet concentrations prepared by standard procedures, which result in undesired immunological response on the part of the patient receiving the platelets. The ultraviolet irradiation of platelet preparations appears to disable the lymphocytes from causing such an undesired immune response. The result of this is to prolong the life of donated platelets in the blood stream of a patient, for example cancer patients undergoing chemotherapy or the like.

As described in the Kahn et al. patent, a platelet suspension in a plastic container, permeable to ultraviolet radiation, is exposed to an ultraviolet dosage. Specifically, a dosage of radiation of about 774 Joules per square meter for about 30 minutes is proposed, using polyethylene, polypropylene, or polyvinyl chloride bags. The ultraviolet radiation passes through the bag walls to irradiate platelets and other cells present, to provide a cell preparation for administration to the patient which elicits little or no undesirable immune response from the patient.

The process of Dr. Kahn has been further improved and refined, particularly through the improvements described in Miripol et al. U.S. Pat. Nos. 4,726,949; 4,952,812; and 4,866,282. Specifically, it was found that improvements in the results can be obtained with an increase in the overall energy of ultraviolet radiation exposure, while improvements in the apparatus for administering ultraviolet radiation to flexible containers of blood product are also disclosed.

In accordance with this invention, improvements are provided in a flexible, flat-collapsible, ultraviolet transparent container for holding the above blood product, any other blood or biological liquid product, or any other material, in sealed manner while it is irradiated with U.V. radiation. Additionally, an improved apparatus for administering such ultraviolet radiation is disclosed.

In the field of collecting and processing blood components for administration to patients, it is of course extremely important to provide proper identification and categorization of the various blood component portions. This has been customarily done in the past by printing indicia on the face and tubing of the bag which contains the blood components. However, with respect to the particular blood component at issue here which is to be irradiated with ultraviolet radiation, printed indicia on the bag will serve to block the ultraviolet irradiation of the contents thereof, resulting in unsuccessful ultraviolet irradiation. Accordingly, it is highly preferable for the container to be free of indicia that would block the ultraviolet irradiation of the blood product contents thereof.

At the same time, it is desirable to have a quick and reliable means for indicating that the blood component within the container has or has not been treated with ultraviolet irradiation. Also, the indicia identifying the container desirably include a bar code so that the container and its contents may be tracked and categorized through a computerized inventory control system, which can reduce the danger of misidentification or loss that is more likely with a manual inventory control system.

Accordingly, there is a need for the container to be automatically and properly positioned in the irradiation device so that a bar code can be automatically read, while at the same time the bar code does not interfere with the ultraviolet irradiation of the contents of the container, and the bar code is not accidently positioned in an ultraviolet irradiation apparatus wrongly, or with a misidentification of the contents of the container, or the like.

The above technical issues are addressed and successfully dealt with in the container of this invention, especially when processed in apparatus as disclosed in this invention, to achieve the many advantages that are available when the above recited technical disadvantages are overcome.

DESCRIPTION OF THE INVENTION

In accordance with this invention, a container is provided for the irradiation of blood or other products. The container comprises a flexible, flat-collapsible wall defining a sealed blood product chamber. Access port means, typically a plurality of conventional access ports, are provided for communicating through the wall to the blood product chamber.

A flap is also provided, integral with the wall and spaced from the chamber. The flap preferably is made of the same, typically transparent plastic material that the rest of the container wall is made of, carrying a label on or within the plastic flap. The label, in turn, carries identifying indicia, typically including bar code indicia.

The container wall is made of a plastic material that is substantially transparent to the specific irradiation being used. In the case of ultraviolet radiation, a suitable plastic material for use is poly(ethylene vinyl acetate). Such materials are readily commercially available, and bags of such material are available from the Fenwal division of Baxter International Inc. of Deerfield, Ill.

It is preferred for the container, and particularly the flap of the container, to carry means for detecting and indicating exposure of the container to the irradiation. Ultraviolet exposure indicating tape or tabs are commercially available, for example from the U.V. Process Supply Co. of Chicago, Ill.

Additionally, it is preferred for the container, typically within the flap, to define alignment hole means spaced from the chamber for facilitating the orientation of the container with apparatus for irradiation, and also apparatus for bar code reading. Thus, a pair of pins may be appropriately positioned in the irradiation apparatus, and a container in accordance with this invention may be mounted on such a pair of pins by means of a pair of alignment holes appropriately positioned in the flap so that, when the container is so mounted on the alignment holes, the bar code on the flap is properly positioned to be read by a bar code reader, and the container is properly positioned for irradiation in the apparatus. The bag flap may also carry an area for receiving handwritten notes or other indicia for added comments and identification by the user.

Thus, a flexible, collapsible container is provided in which the wall of the container which defines a blood product chamber is at least substantially free of opaque indicia to facilitate the irradiation thereof, while the identifying and describing indicia, typically including a bar code, are positioned on a flap which is spaced from the blood product chamber defined by the container.

Additionally, the container can be quickly examined to determine whether it has been exposed to radiation or not by means of the means for detecting and indicating such exposure, and alignment hole means are provided for assuring proper alignment of the container for appropriate irradiation and bar code reading.

While the container of this invention may be used in conjunction with a large variety of different apparatus for irradiation, the container is preferably used with apparatus for irradiating with ultraviolet radiation a layer of blood product containing white cells, the layer being defined by the container as it lies on a tray within the apparatus. The apparatus comprises a housing which defines a chamber and a pair of ultraviolet light sources positioned on opposed sides of the chamber. The housing comprises a pair of housing sections which are moveable in hinged relation between opened and closed positions, each of the sections carrying one of the pair of ultra violet light sources. A manually removable tray is carried within the housing to define a support surface for a flexible container of blood product, such as, but not limited to, the container as described herein. Thus, such a flexible container may be carried in the chamber. The support surface of the tray is made of an ultraviolet-transmissive material such as quartz, so that the container may be irradiated from both sides of the tray by the pair of ultraviolet light sources.

Additionally, the apparatus may carry a bar code reader which is positioned to read bar codes carried on flaps of containers made in accordance with this invention. Typically, the tray carries pin means which are positioned to engage alignment hole means in the containers to be irradiated, so that the container is appropriately aligned for both irradiation and bar code reading.

DESCRIPTION OF SPECIFIC EMBODIMENTS

Figure 1:
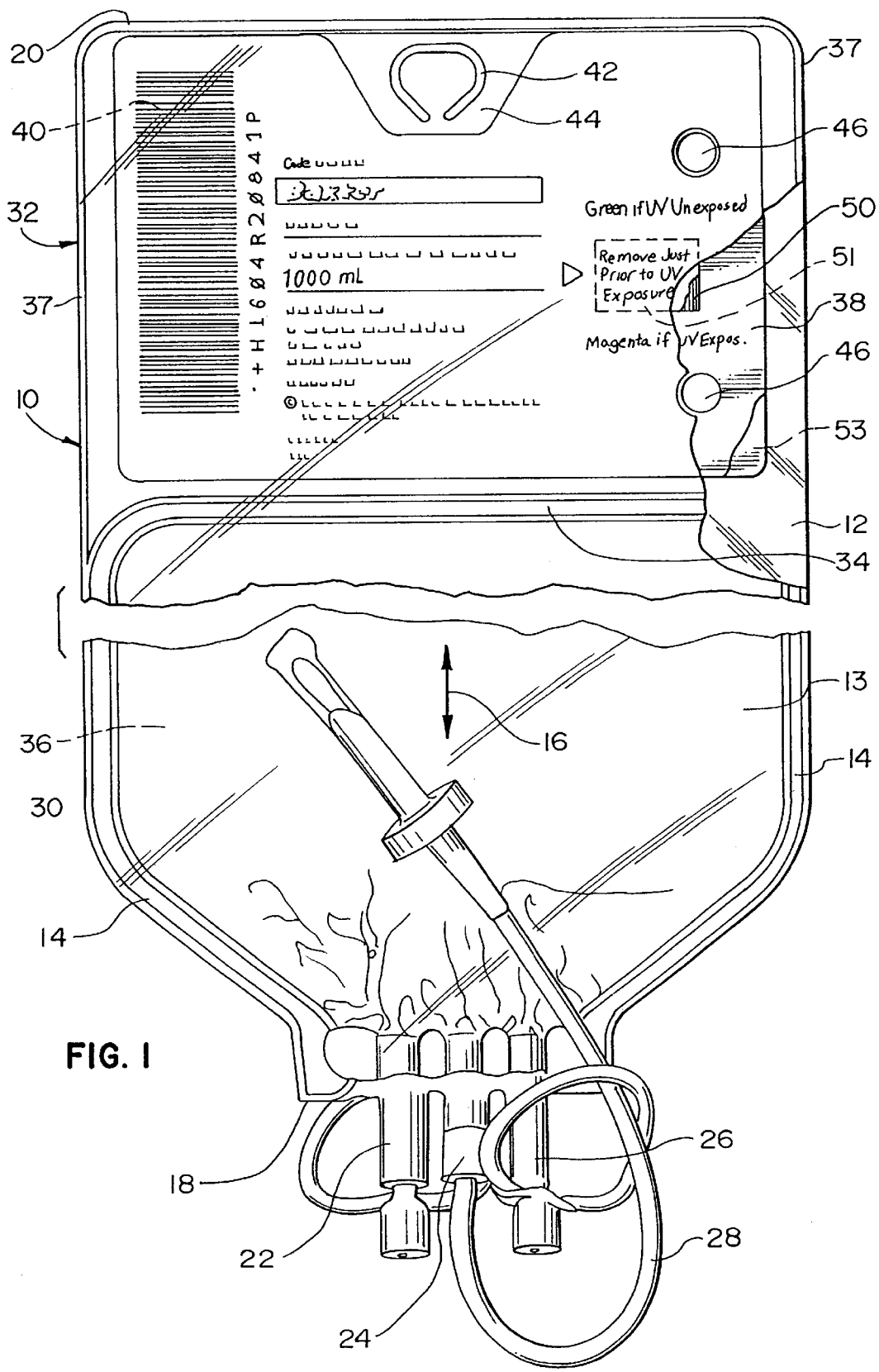
FIG. 1 is a front plan view of a flexible, collapsible container for the irradiation of blood products in accordance with this invention, with portions broken away.

Referring to FIG. 1, a flexible, collapsible container 10 for the irradiation of blood is disclosed. Container 10 may be made in accordance with substantially conventional design, except as otherwise described herein, being made of a pair of peripherally heat sealed sheets of poly (ethylene vinyl acetate) 12, 13, peripherally sealed together by a radio frequency heat seal or other type of seal line 14.

Container 10 defines a major longitudinal axis 16 between container ends 18, 20, with three access ports 22, 24, 26 being defined at one end thereof in conventional manner. Central access port 24 connects to a short length of flexible tubing 28, which terminates in a conventional spike connector 30. The other two access ports are connected to short, semi-rigid, tubular ports containing a spike puncturable diaphragm in conventional manner, being closed by conventional D-ring port protectors as described, for example, in U.S. Pat. No. 4,573,980 and as commercially used on other medical containers.

At the end 20 of container 12, a flap 32 is defined, being spaced from the chamber 36 defined within peripheral seal line 14 by peripheral seal line portion 34. Flap 32 may be made from an integral piece of plastic sheets 12, 13, being connected by another peripheral seal line 37 to carry a printed label or card 38 on or within flap 32. As shown, printed label 38 carries various desired indicia, including a bar code 40, which is readable by a conventional bar code reader through the transparent plastic of plastic layer 13.

Hanger hole 42 may be cut out of the two joined plastic layers 12, 13, and reinforced by an extension 44 of the peripheral seal line 37 about flap 32.

Flap 32 also defines a pair of punched holes 46, which are positioned to be received on prongs or rods carried in the irradiation apparatus for which container 10 is made, to properly position container 10 in a manner so that bar code 40 is read by a bar code reader carried in the irradiation apparatus, and also to assure proper positioning of chamber 36 for proper ultraviolet irradiation.

Additionally, flap 32 may carry a small amount of ultraviolet sensitive color label or tape 50, which tape is commercially available and which changes color upon substantial ultraviolet exposure. Tape 50 is positioned on the outer surface of plastic layer 13, and may be protected by a protective flap 51, which is removed prior to ultraviolet exposure. For example, one commercially available ultraviolet indicator tape is green if unexposed, but turns to magenta if exposed to substantial ultraviolet radiation.

On the reverse side of flap 32, a paper label 53 may be adhered to the outer surface of plastic layer 12, to permit the user to write notes or indicating indicia with a pen or pencil.

It can be seen that the bulk of container 10, particularly the container walls surrounding chamber 36, is free of any opaque indicia, with all of the indicia being carried in the flap. Thus, there is no interference with the ultraviolet irradiation of the contents of the container.

Figure 2:
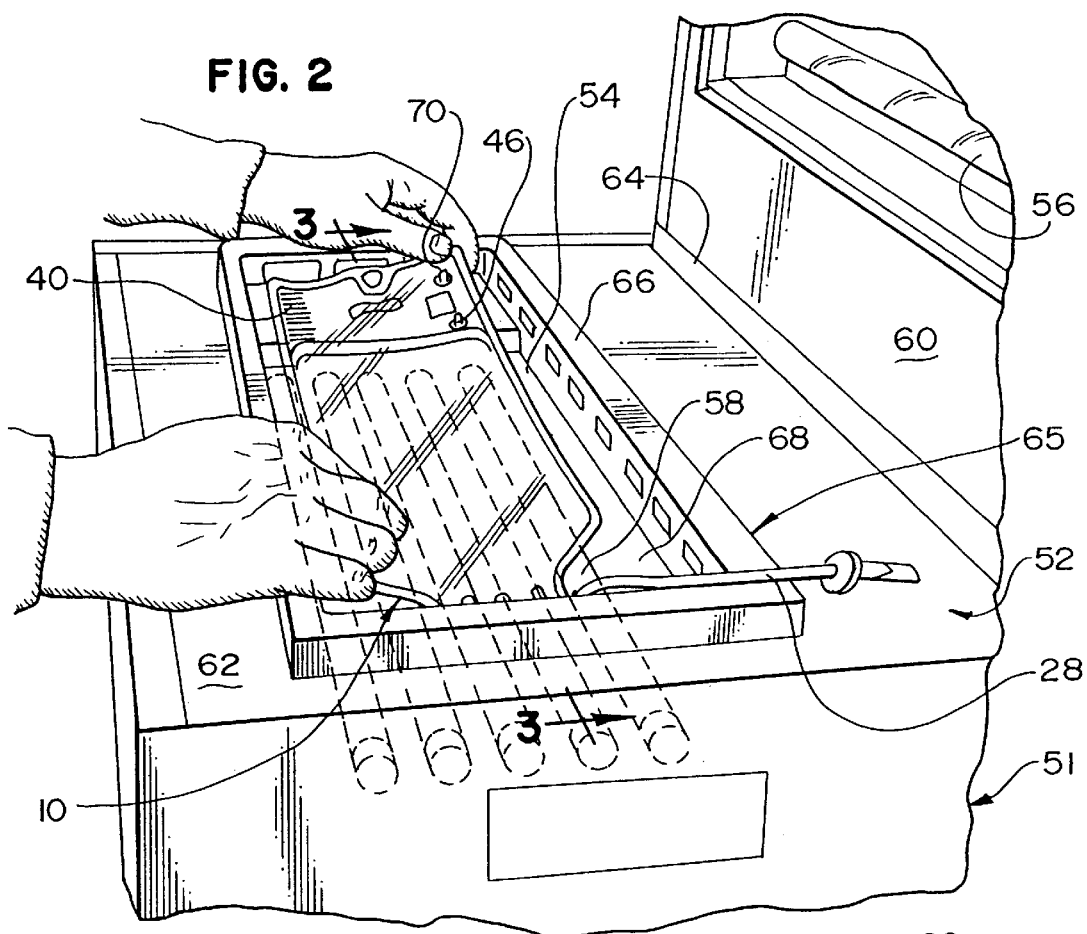
FIG. 2 is a perspective view showing bag irradiating apparatus in open position.
Figure 3:
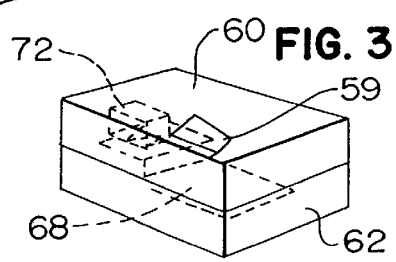
FIG. 3 is a perspective view showing the apparatus of FIG. 2 in closed position.
Figure 4:
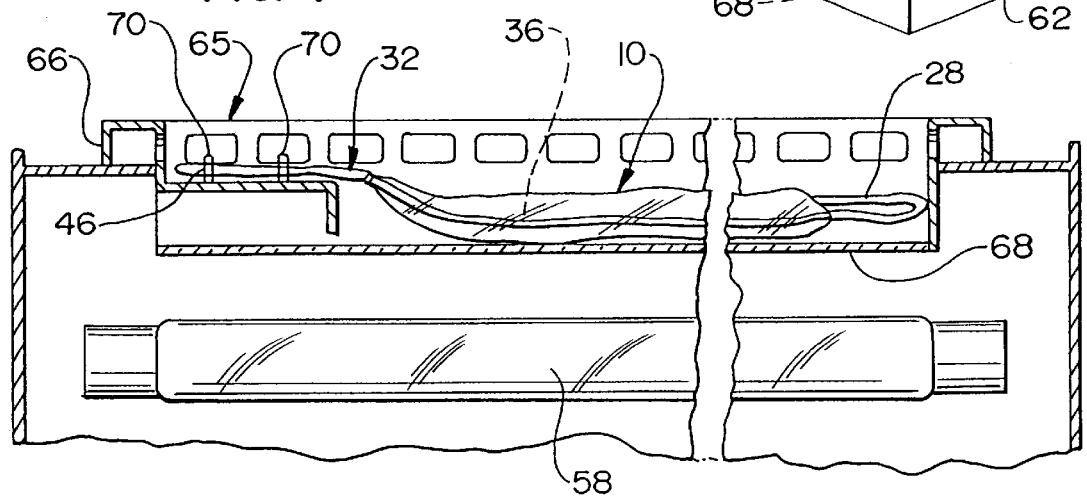
FIG. 4 is a sectional view taken along line 3—3 of FIG. 2 showing the manually removable, internal tray of the apparatus receiving a flexible, collapsible container of blood product.

Turning to FIGS. 2–4, an apparatus for the irradiation of the container of FIG. 1 is disclosed. Apparatus 51 comprises a housing which defines an internal chamber 54, with banks of ultraviolet lights 56, 58 carried on opposed sides of chamber 54 by the housing.

Housing 52 comprises a pair of housing sections 60, 62 which are connected together on one side with hinges 64 so that the housing sections are movable in hinged relation between an open position as shown in FIG. 3 and a closed position as shown in FIG. 4, with the ultraviolet irradiation taking place in the closed position. Each of sections 60, 62 carries one of the banks of ultraviolet lights 56, 58 plus conventional circuitry for operating them, being connected to a control panel 59 carried on the apparatus.

A manually removable tray 65 is provided to fit within the housing sections of apparatus 51 when the apparatus is in its closed position. Thus, the apparatus can be opened, and the tray 65 may be removed and replaced with ease, the tray being appropriately positioned so that both sides of it are irradiated by the ultraviolet light banks 56, 58.

Tray 64 defines a frame 66 and a bottom wall or floor 68, the later being made of quartz to be ultraviolet transmissive. Thus, a flexible, collapsible container 10 such as that shown in FIG. 1 may be placed on the floor 68 of the tray to form a layer of blood product which is spread out to the degree permitted by the flexible collapsible container. Then, tray 65 is placed into irradiation apparatus 51 while the apparatus is in open position, and then the housing sections 60, 62 may be closed by pivotable hinged motion into their closed configuration as in FIG. 3. The ultraviolet light banks are then actuated for a predetermined time as set by means of the apparatus controls.

Tray 65 defines a set of pins 70 which may be positioned to pass through holes 46 of collapsible container 10 to properly position the container within apparatus 51. Thus, with such proper positioning, chamber 36 is properly positioned for optimum exposure to ultraviolet light from light banks 56, 58, while bar code 40 is positioned for proper reading by a bar code reader 72, carried by housing section 60. The protective cover 51 is removed from ultraviolet sensitive tape 50 prior to the ultraviolet irradiation.

Thus, through a software driven system which may be included in or connected to apparatus 51, the bar code reader can cross check with other data to be sure that the contents of bag 10 are being properly treated, and that the identity of the contents of bag 10 has been verified. Appropriate information from the bar code can be read out or printed out for the users as may be desired. The system may be disabled if the bar code is not that which was expected by the program.

After the ultraviolet irradiation has taken place, apparatus 51 may be opened, and tray 64 may be removed, for the easy removal of container 10, and optional replacement with another container 10 containing another portion of blood product.

Thus, ultraviolet irradiating apparatus and a container for use therein is disclosed, having significant advantages based on automated monitoring of the identity of the blood product being irradiated, for added reliability of identification of the blood product, to further provide the confidence that blood products will not become mixed up or processed wrongly. Additionally, one can tell from a glance whether the container has been U.V. irradiated or not, as a further cross check against undesired double irradiation or failure to irradiate. At the same time, while all desired identifying indicia may be applied to the bag, the chamber that holds the blood product is not shadowed and shielded from ultraviolet irradiation by any indicia carried on the wall that surrounds the chamber.

The above has been offered for illustrative purposes only, and is not intended to limit the scope of the invention of this application, which is as defined in the claims below.

That which is claimed is:

1. Apparatus for irradiating materials, which comprises:
 a housing which defines a chamber and a pair of ultraviolet light sources positioned on opposed sides of said chamber, said housing comprising a pair of housing sections moveable in hinged relation between open and closed positions, each section carrying one of said pair of said ultraviolet light sources;
 a manually removable tray carried within said housing to define a support surface for a flexible container in said chamber, said support surface being made of an ultraviolet-transmissive material.

2. The apparatus of claim 1 in which each ultraviolet light source comprises a plurality of ultraviolet light bulbs.

3. The apparatus of claim 1 which includes means for reading a bar code carried on a flexible, collapsible container.

4. The apparatus of claim 3 in which said manually removable tray carries pin means for passing through preformed holes in said flexible, collapsible container to locate the container in a manner for optimum ultraviolet radiation of the container and reading of said bar code.

* * * * *